United States Patent [19]

Bend et al.

[11] 4,256,646
[45] Mar. 17, 1981

[54] SYNTHESIS OF OPTICALLY PURE THROMBOXANES

[75] Inventors: Oscar Hernandez, Cary, N.C.; John R. Bend; Thomas E. Eling; James D. McKenney, all of Raleigh, N.C.

[73] Assignee: The United States of America as represented by the Department of Health, Education and Welfare, Washington, D.C.

[21] Appl. No.: 30,315

[22] Filed: Apr. 16, 1979

Related U.S. Application Data

[63] Continuation-in-part of Ser. No. 920,392, Jun. 29, 1978, abandoned.

[51] Int. Cl.³ .......................................... C07D 309/22
[52] U.S. Cl. ...................... 260/345.8 P; 260/345.7 P; 260/345.8 R; 260/345.9 P; 260/345.9 R; 260/343.6
[58] Field of Search .................. 260/345.9 P, 345.8 P, 260/345.7 P, 345.8 R

[56] References Cited

U.S. PATENT DOCUMENTS 3,998,852 12/1976 Alvarex et al. .............. 260/345.8 P
4,052,552 10/1977 Schneider ....................... 260/345.7 P

OTHER PUBLICATIONS

Hernandez, Tetrahedron Letters, No. 3, 219-222 (1978).
Kelly et al., Tetrahedron Letters, No. 37, 3279-3282 (1976).
Anderson et al., Jacs, 97, 3870 (1975).
Hicks et al, Jcs Chem. Comm., 869 (1976).
Nelson et al., Tetrahedron Letters, No. 37, 3275-3278 (1976).
Sneider et al., Tetrahedron Letters, No. 37, 3283-3286 (1976).
Corey et al., Jacs, 93, 1491 (1971).

*Primary Examiner*—Nicky Chan
*Attorney, Agent, or Firm*—John S. Roberts, Jr.

[57] ABSTRACT

In an elegant stepwise process for the production of intermediates of thromboxanes such as TXB₂ from a chiral glucose starting material such as α-methylglucoside, those steps comprising:

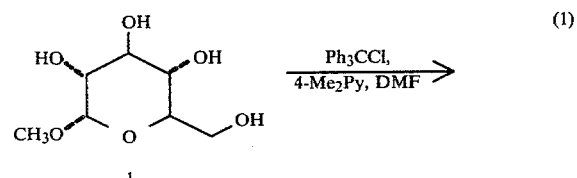

(1)

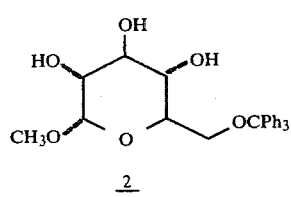

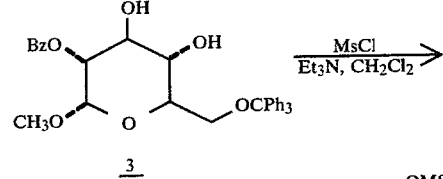

(2)

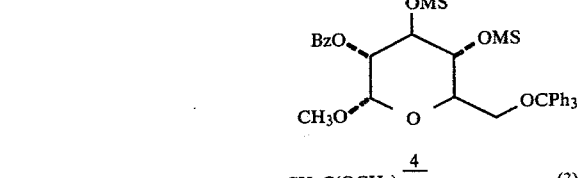

(3)

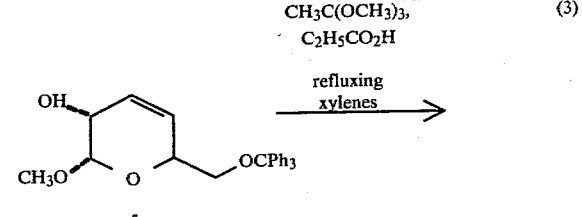

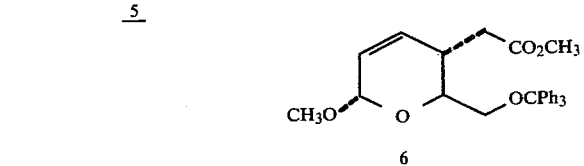

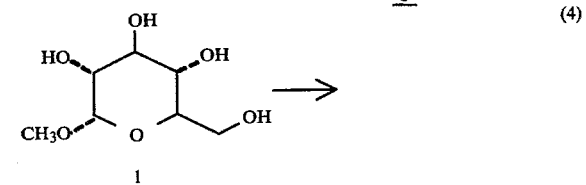

(4)

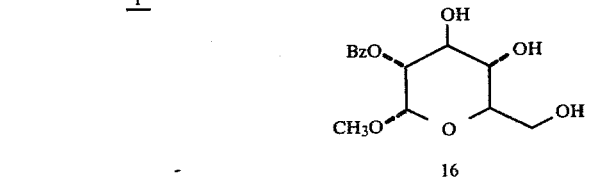

(5)

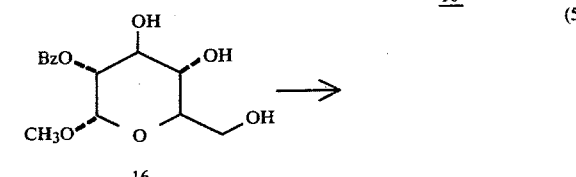

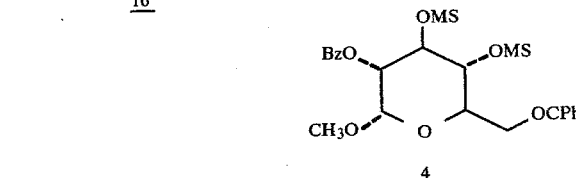

A key modification introduced in this synthetic sequence is the use of 4-dimethylaminopyridine for the selective alkylation of primary alcohols in the presence of unprotected secondary alcohols and for the controlled acylation of methylglucoside. The former application has large potential use in the synthesis of nucleosides, polynucleotides, and carbohydrate derivatives.

2 Claims, No Drawings

SYNTHESIS OF OPTICALLY PURE THROMBOXANES

This application is a continuation-in-part application of pending Ser. No. 920,392 filed June 29, 1978, now abandoned.

The prostaglandins are a family of biologically potent lipid acids first discovered in semenal fluid and extracts of accessory genital glands of man and sheep. Related to these prostaglandin are the compounds of the present invention; namely, thromboxane $B_2$ intermediates. These thromboxane $B_2$ are obtained from prostaglandins endoperoxides $PGG_2$ and $PGH_2$ which are metabolized in human platelets to a new group of biologically active compounds called here thromboxanes. These thromboxane compounds and their analogs show utility for biomedical research as, for example, clotting agents. Thromboxane $A_2$ ($TXA_2$) has been suggested to play a critical role in platelet aggregation. $TXA_2$ is unstable in aqueous solution and it is rapidly hydrolyzed to thromboxane $B_2$ ($TXB_2$).

A structure for thromboxane $TXB_2$ is as follows:

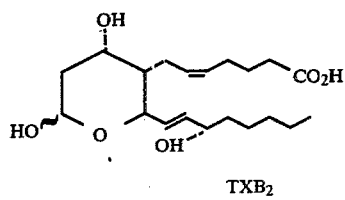

TXB$_2$

The lack of availability of these compounds as agents in prostaglandins biosynthesis was a starting point for a synthesis of the thromboxane intermediates. A major problem in working with racemic materials is the loss usually associated with the optical resolution of the desired intermediate. The use of carbohydrates as optically pure precursors has been demonstrated by Fraser-Reid, post. An intermediate was prepared such as 9 (see schemat below) from which $TXB_2$ can be synthesized by following the methodology perfected by Corey, post, for the synthesis of prostaglandins. The publication of a series of papers on the synthesis of $TXB_2$ under the auspices of the Upjohn Company is noted in the prior art below. (See Nelson et al, Kelly et al, and Schneider et al in *Tetrahedron Letters*.)

PRIOR ART STATEMENT

N. S. Nelson and R. W. Jackson, *Tetrahedron Letters*, 3275 (1976).

R. C. Kelly, I. Schletter, and S. J. Stein, *Tetrahedron Letters*, 3279 (1976).

W. P. Schneider and R. A. Morge, *Tetrahedron Letters*, 3283 (1976).

O. Hernandez, *Tetrahedron Letters*, No. 3, 219–222 (1978).

R. C. Anderson and B. Fraser-Reid, *J. Am. Chem. Soc.*, 97:3870 (1975).

D. R. Hicks and B. Fraser-Reid, *J.C.S. Chem. Comm.*, 869 (1976).

E. J. Corey et al, *J. Am. Chem. Soc.*, 93:1491 (1971).

S. Chaudhary and O. Hernandez, "A Simplified Procedure for the Synthesis of Triphenylmethylethers," *Tetrahedron Letters* (in press).

S. Chaudhary and O. Hernandez, "4-Dimethylaminopyridine: An Efficient and Selective Catalyst for the Silylation of Alcohols, "*Tetrahedron Letters* (in press).

Detailed preparations of compounds 2, 4, and 6 appear post in the examples and in the text of the specification. Furthermore, relative to protective groups generally as in 16 with BzO-, the present authors describe the use of another versatile protective group, the t-butyl dimethylsilylether group; cf. the Chaudhary et al article on the silylation of alcohols noted above.

The protection of the OH by conventional etherification to BzO- in the mini-schemat 1→16→4 and producing 2-O-benzoyl glucopyranoside (16) protects the 2-position for later presence in the sequence.

A schemat for the synthesis applicable to these intermediates in the production of thromboxanes is as follows:

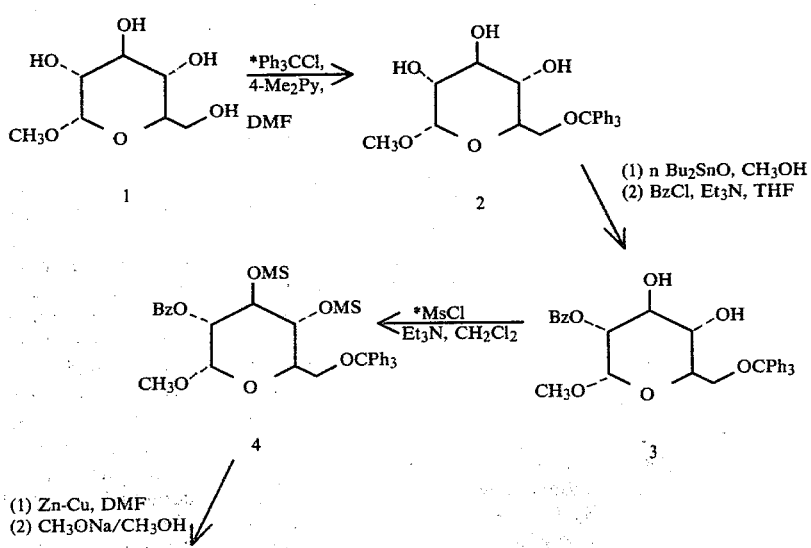

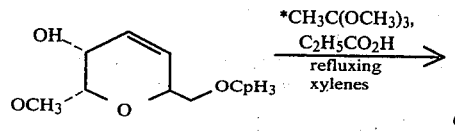 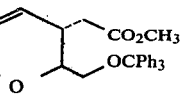

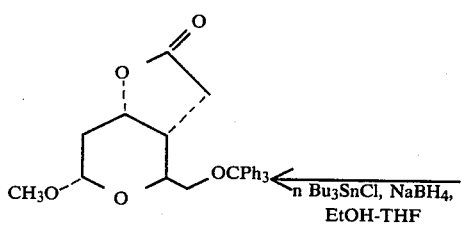 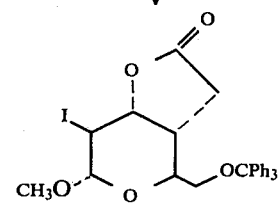

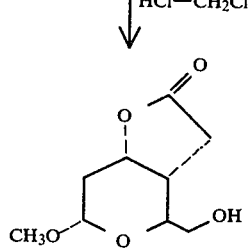

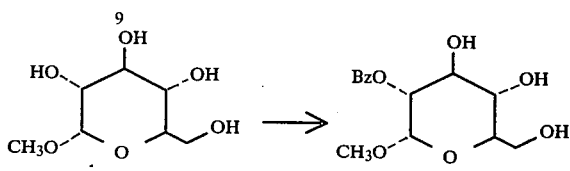

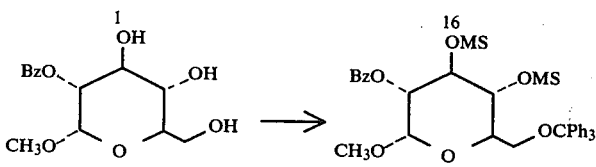

Intermediates similar to 9 were successfully transformed to TXB$_2$. In the present invention there is described a stereo-selective, chiral synthesis of compound 9 starting with commercially available α-methylglucoside (1). In addition to this, D-glucose sugars such as D-galactose and D-mannose are useful as starting materials. The strategy features the sequential activation of the hydroxyl groups of glucose, culminating with the introduction of the acetic acid side chain at C-4 (glucose numbering) in a stereochemically predictable manner. E. J. Corey et al, supra, describe a process similar to the present invention but lacks several of the effective steps. Reaction of methyl-α-D-glucopyranoside (1) with triphenylmethyl chloride (triethylamine, dimethylformamide, catalytic amount of 4-dimethylaminopyridine) gave the tritylether 2 (85%), mp 154.5°-155.5°; m/e 436 (M+), 404 (M+—CH$_3$OH), 359 (M+—C$_6$H$_5$). Selective activation of the hydroxyl group at C-2 was achieved by formation of the di-n-butylstannylene derivative (di-n-butyltinoxide, refluxing methanol), which was subsequently transformed (benzoyl chloride, triethylamine, tetrahydrofuran) to 3 methyl-2-O-benzoyl-6-O-trityl-α-D-glucopyranoside (85%), mp 93°-95°, [α]$_D$+120° (c, 2), m/e 540 (M+), 508 (M+—32). Reaction of 3 with methanesulfonyl chloride (triethylamine, dichloromethane) gave the dimesylate 4 (80%), mp 174.5°-176.5°, m/e 696 (M+), 619 (M+—C$_6$H$_5$). Treatment of 4 with zinc-copper couple and potassium iodide in refluxing dimethylformamide produced a mixture wherein the substituent at the 2 position is either OH or BzO. The desired substituent OH at the 2 position is achieved by tran-esterification (sodium methoxide, dichloromethane-methanol) and afforded pure 5 methyl-3,4-dideoxy-6-O-trityl-hex-3-enpyranoside (75%), mp 123°–125°; m/e 502 (M+), 460 (M+—CH$_3$OH). The allylic alcohol 5 when subjected to the conditions of the orthoester Claisen rearrangement [cf. J. Am. Chem. Soc. 92:741 (1974)] (trimethylorthoacetate, propionic acid, refluxing xylene) was transformed to the ester 6 (65%) mp 78°–80°; [α]$_D$+90° (c, 1.1); m/e 458 (M+), 426 (M—CH$_3$OH). Alkaline hydrolysis (sodium hydroxide, aqueous tetrahydrofuran) of 6 followed by reaction with potassium iodideiodine in 0.5 M sodium bicarbonate gave the iodolactone 7 (90%) mp 221°–223°; [α]$_D$+42° (c, 0.8), m/e 570 (M+), 493 (M+—C$_6$H$_5$). Reduction of 7 with tri-n-butyltin hydride (nBu$_3$SnCl, NaBH$_4$, 50% ethanol-tetrahydrofurane) afforded the highly crystalline lactone 8 (95%), mp 241°–243°; [α]$_D$+78° (c, 0.5); m/e 444 (M+), 412 (M+—CH$_3$OH). Removal of the trityl group (hydrogen chloride, dichloromethane) yielded the desired intermediate hydroxylactone 9 (85%), mp 102°–103°; [α]$_D$+85 (c, 0.5; m/e 202 (M+), 170 (M+—CH$_3$OH). The infrared and nuclear magnetic resonance spectra of 9 were identical to those of an authentic sample provided by the Upjohn Company. The subsequent steps leading to TXB$_2$ are deemed conventional and described in the literature: Nelson et al, Tetrahedron Letters, 3275 (1976); Kelly et al, Tetrahedron Letters, 3279 (1976); and Corey et al, Tetrahedron Letters, 1625 (1977). For purposes of novelty the steps in the flow chart from 1→2 from 3→4, from 5→6 and the sequence 1→16→4 are deemed novel.

The following abbreviations are utilized in the specification and claims:
Ph, phenyl; MS, methanesulfonyl; Bz, benzoate; THF, tetrahydrofurane; DMF, N,N-dimethylformamide; DME, 1,2-dimethoxyethane; DMSO, dimethylsulfoxide; 4-Me$_2$Py, 4-dimethylaminopyridine.

EXAMPLE 1

Production of 6-O-trityl-α-methylglucoside (Compound 2)

In analogy with established mechanism for the pyridine catalyzed transfer of acyl groups, one can assume that the tritylation reaction proceeds by initial formation of N-tritylpyridinium salt from which the alkyl group is transferred to the alcohol. The formation of this pyridinium salt is rate determining and consequently the high reactivity of N-tritylpyridinium fluoroborate can be explained in this manner. In the present reaction tritylchloride in 1.1 equivalent with α-methylglucoside are reacted in N,N-dimethylformamide (DMF) solution overnight at room temperature (et) in the presence of 4-N,N-dimethylaminopyridine (DAP) (0.04 equivalents) and triethylamine (1.5 equivalents) cleanly produced 6-O-triethyl-α-methylglucoside, Compound 2, at 88% yield.

EXAMPLE 2

Methyl-2-O-benzoyl-3,4-di-O-methanesulfonyl-6-O-trityl-α-D-glucopyranoside (Compound 4)

A mixture of methyl-2-O-benzoylglucopyranoside (Compound 16, 11.96 g, 40 mmol), triphenylmethylchloride (44 mmol, 12.3 g), triethylamine (60 mmol, 8.4 ml), and 4-dimethylaminopyridine (2 mmol, 244 mg) was dissolved in dry DMF (150 ml) and stirred overnight at room temperature under argon. After 16 hrs reaction tlc (silica gel, ethylacetate) showed no starting material. The pale yellow solution was diluted with dry dichloromethane (50 ml), triethylamine (90 mmol, 13 ml) added and the resulting mixture was cooled to −25°. A solution of methane sulfonylchloride (90 mmol, 7.5 ml) in dichloromethane (100 ml) was added dropwise over a period of one hour. The mixture was allowed to warm to room temperature and stirring continued for one hour. Extractive work-up using water, 5% HCl, saturated sodium bicarbonate, and drying the organic solution with sodium sulfate provided a brownish oil. This crude product was dissolved in a small volume of benzene and filtered through a silica gel column. Elution with hexane gave mostly triphenylmethanol, elution with ethylacetate gave 21 g (74%) of 4 which was recrystallized from ethermethanol, mp 175°–177°.

EXAMPLE 3

Methyl-2,3,4-trideoxy-6-O-trityl-4-methylcarboxymethylhex-2-enpyranoside (Compound 6)

A mixture of allylic alcohol 5 (4 g), trimethylorthoacetate (3 ml), and propionic acid (0.5 ml) in dry xylene (30 ml) were refluxed under argon with continuous distillation of methanol. The course of the reaction was monitored by thin-layer chromatography (cyclohexaneethylacetate, 3:1; silica gel). After one hour reaction additional propionic acid (0.25 ml) and trimethylorthoacetate (1 ml) were added and reflux was continued for 2 hr. The reaction mixture was filtered through a short alumina column (activity III) and eluted with hexane. The sample was purified by preparative HPLC (silica gel, 2% ethylacetate/dichloromethane) in a Water Prep 500 liquid chromatograph. Evaporation of the solvent gave 6 (3.1 g, 65% yield) which, after recrystallization from ethanol, had mp 78°–80°. Other physical constants described in Tetrahedron Letters, 219°–222 (1978).

EXAMPLE 4

Utilization of an Alternative Silylation Agent

In addition to the preferred practices of the present invention, an additional protective group which may be utilized is tert-butyldimethylsilyl (TBDMS) which, when used in conjunction with 4-dimethylaminopyridine (DAP) as a group transfer agent in the triphenylmethylation of alcohols, has been found to be very effective.

TABLE 1

Formation of TBDMS Ethers From Primary and Secondary Alcohols by the TBDMCS-DAP Procedure

| Alcohol | DAP (eq)[a] | Reaction Conditions | TBDMS ether Yield (%)[b] |
|---|---|---|---|
| PhCH$_2$OH | 0.04 | CH$_2$Cl$_2$, 25° | 89 |
| (HO—furanose—Ur, HO OH) | 0.24 | DMF, 25° | 60[c] |
| (cholesterol, C$_8$H$_{17}$, HO) | 0.33 | CH$_2$Cl$_2$, 25° | 68 |
| (tBu-cyclohexanol-OH, cis and trans) | 0.33 | DMF, 25° | 85[d] |

[a]TBDMCS (1.1 eq) and triethylamine (1.2 eq) used.
[b]Yields are for purified samples.
[c]5-0′-TBDMS-uridine.
[d]74% equatorial and 26% axial isomer by GC analysis.

EXAMPLE 5

Preparation of Compound 16

Methyl-α-D-glucopyranoside (1, 0.1 mol, 19.4 g) and di-n-butyltinoxide (0.1 mol, 25 g) were refluxed in dry methanol (450 ml) under nitrogen atmosphere for 3 hr. The mixture was cooled to 10° (ice-bath) and triethylamine (distilled, 0.5 mol, 50.5 g, 70 ml) was added in one portion, followed by benzoylchloride (0.5 mol, 71 g, 59 mol) dropwise over a period of 7 hr. After stirring one more hour at 10°, the mixture was allowed to warm to room temperature and stirring continued overnight (14 hr). The resulting precipitate was filtered and washed with ethylacetate (100 ml×2) and the combined organic solutions evaporated to dryness. The solid obtained was chromatographed on silica gel (Waters Associates Prep-500) using ethylacetate as eluent to provide 24 g (80% yield) of pure 16.

Preparation of Compound 4

A solution of compound 1 (26.9 g, 61.7 mmol) in dichloromethane (300 ml), 4-dimethylaminopyridine (300 mg, 2.5 mmol) was cooled in an ice-bath (4°–6°) and triethylethylamine (80 mmol, 12 ml) was followed by dropwise addition of benzoylchloride (74 mmol, 8.6 ml) in dichloromethane (50 ml). After 1 hr at 4° the mixture was allowed to warm to room temperature and stirring continued for 1 hr. Analysis by tlc (silica gel, ethylacetate) showed no starting material remaining. Triethylamine (160 mmol, 24 ml) was added and the mixture cooled to −25°. Methane sulfonylchloride (120 mmol, 12 ml) in dichloromethane (50 ml) added dropwise in 1 hr and the resulting mixture was allowed to stand in a freezer (−25°) overnight. Aqueous work-up provided a solid which was chromatographed (Waters Prep 500) on silica gel using ethylacetate as eluent to provide 32 g (75%) of pure 4, mp 175°–77°.

We claim:

1. A process of producing compound 6 (methyl-2,3,4-trideoxy-6-O-trityl-4-methylcarboxymethyl-hex-2-enpyranoside) comprising reacting compound 1 (methyl-α-D-glucopyranoside) in the presence of $Ph_3CCl$ and 4-$Me_2Py$ and DMF to produce compound 2 (6-O-trityl-α-methylglucoside) and reacting compound 2 in the presence of n-$Bu_2SnO$, $CH_3OH$ and BzCl, $Et_3N$, THF to produce compound 3 (methyl-2-O-benzoyl-6-O-trityl-α-D-glucopyranoside) and reacting compound 3 in the presence of MsCl and $Et_3N$, $CH_2Cl_2$ to produce compound 4 (methyl-2-O-benzoyl-3,4-di-O-methanesulfonyl-6-O-trityl-α-D-glucopyranoside) and reacting compound 4 in the presence of Zn-Cu, DMF and $CH_3ONa/CH_3OH$ to produce compound 5 (methyl-3,4-dideoxy-6-O-trityl-hex-3-enpyranoside) and reacting compound 5 in the presence of $CH_3C(OCH_3)_3$, $C_2H_5CO_2H$ while refluxing xylenes to produce the desired compound 6 (methyl-2,3,4-trideoxy-6-O-trityl-4-methylcarboxymethyl-hex-2-enpyranoside).

2. The process according to claim 1 wherein the steps consist of producing compound 4 (methyl-2-O-benzoyl-3,4-di-O-methanesulfonyl-6-O-trityl-α-D-glucopyranoside) by reacting compound 1 (methyl-α-D-glucopyranoside) with benzoyl chloride to form compound 16 (methyl-2-O-benzoyl glucopyranoside) and subsequently reacting compound 16 to form compound 4.

UNITED STATES PATENT OFFICE
CERTIFICATE OF CORRECTION

Patent No. 4,256,646     Dated March 17, 1981

Inventor(s) HERNANDEZ, BEND, ELING and McKENNEY

It is certified that error appears in the above-identified patent and that said Letters Patent are hereby corrected as shown below:

On the title page of the Letters Patent, left column, above the title line: change "Bend et al." to --Hernandez et al.-- to reflect the name of the primary inventor rather than the second inventor.

*Signed and Sealed this*

*Twentieth* Day of *April 1982*

|SEAL|

*Attest:*

GERALD J. MOSSINGHOFF

*Attesting Officer*     *Commissioner of Patents and Trademarks*